United States Patent
Makdissi et al.

(10) Patent No.: US 11,691,020 B2
(45) Date of Patent: Jul. 4, 2023

(54) AUTONOMOUS CARDIAC IMPLANT OF THE LEADLESS CAPSULE TYPE, COMPRISING AN INTERFACE FOR EXTERNAL COMMUNICATION DURING TRANSPORTATION AND STORAGE

(71) Applicant: CAIRDAC, Antony (FR)

(72) Inventors: Alaa Makdissi, Paris (FR); Willy Regnier, Longjumeau (FR); An Nguyen-Dinh, La Riche (FR)

(73) Assignee: Cairdac, Anthony (FR)

( * ) Notice: Subject to any disclaimer, the term of this patent is extended or adjusted under 35 U.S.C. 154(b) by 45 days.

(21) Appl. No.: 17/487,980

(22) Filed: Sep. 28, 2021

(65) Prior Publication Data
US 2022/0203101 A1   Jun. 30, 2022

(30) Foreign Application Priority Data
Dec. 28, 2020   (EP) .................................... 20315507

(51) Int. Cl.
  *A61N 1/378*   (2006.01)
  *A61N 1/375*   (2006.01)
  (Continued)

(52) U.S. Cl.
  CPC ......... *A61N 1/3785* (2013.01); *A61N 1/0565* (2013.01); *A61N 1/3756* (2013.01);
  (Continued)

(58) Field of Classification Search
  CPC .. A61N 1/3787; A61N 1/3727; A61N 1/3785; A61N 1/37205; A61N 1/37512;
  (Continued)

(56) References Cited

U.S. PATENT DOCUMENTS 4,906,870 A * 3/1990 Gongwer ........... H03K 19/0016
                                                  326/39
2012/0294386 A1* 11/2012 Ghovanloo .......... A61N 1/3727
                                                  375/295
(Continued)

FOREIGN PATENT DOCUMENTS

EP   2 857 065 A1   4/2015
EP   3 693 56 A1    8/2020
(Continued)

OTHER PUBLICATIONS

The European 71.3 Notification dated Aug. 10, 2022 for European Application No. 201315507.2.
(Continued)

*Primary Examiner* — Catherine M Voorhees
(74) *Attorney, Agent, or Firm* — Haverstock & Owens, A Law Corporation

(57) ABSTRACT

The implant comprises a tubular body housing an energy harvesting module adapted to convert external stresses applied to the implant into electrical energy, and a rechargeable battery adapted to be charged by the energy harvesting module. During the storage, an external source physically separated from the implant is coupled to the implant rechargeable battery to maintain a minimum battery charge level. An interface circuit of the implant couples surface electrodes to the battery, with switching between: i) a transport and storage configuration where the electrodes are connected to the external source to receive from the latter a battery charging energy and/or to exchange communication signals with the outside through the wire link of the coupling; and ii) a functional configuration in which the surface electrodes are decoupled from the external source after the implant has been implanted. The implant further comprises a data transmitter circuit adapted, in the transport and storage configuration, to send communication signals, via (Continued)

84: External Interface Circuit
86: Internal Interface Circuit the surface electrodes, on the link coupling to the external source, and/or a data receiver circuit adapted, in the transport and storage configuration, to receive, via the surface electrodes, communication signals transmitted on the link coupling to the external source.

12 Claims, 5 Drawing Sheets

(51) Int. Cl.
*A61N 1/05* (2006.01)
*A61N 1/372* (2006.01)
*H02J 7/32* (2006.01)
*A61N 1/36* (2006.01)

(52) U.S. Cl.
CPC ....... *A61N 1/3787* (2013.01); *A61N 1/37205* (2013.01); *A61N 1/37223* (2013.01); *A61N 1/37512* (2017.08); *H02J 7/32* (2013.01); *A61N 1/36139* (2013.01); *A61N 1/3727* (2013.01); *A61N 1/37229* (2013.01)

(58) Field of Classification Search
CPC .............. A61N 1/3756; A61N 1/36139; A61N 1/37229; H02N 2/186
See application file for complete search history.

(56) References Cited

U.S. PATENT DOCUMENTS

| | | | |
|---|---|---|---|
| 2015/0094786 A1* | 4/2015 | Deterre | A61N 1/3785 |
| | | | 310/309 |
| 2015/0174412 A1* | 6/2015 | Stahmann | A61N 1/3756 |
| | | | 607/59 |
| 2017/0180887 A1* | 6/2017 | Meskens | A61N 1/3787 |
| 2018/0008206 A1* | 1/2018 | Stahmann | A61N 1/3925 |
| 2019/0091479 A1* | 3/2019 | Bonnet | A61N 1/3975 |
| 2022/0203102 A1* | 6/2022 | Makdissi | A61N 1/37205 |

FOREIGN PATENT DOCUMENTS

| | | | | |
|---|---|---|---|---|
| EP | 3 708 221 A1 | 9/2020 | | |
| WO | 98/08567 A1 | 3/1998 | | |
| WO | WO-9808567 A1 * | 3/1998 | ............. | A61N 1/378 |

OTHER PUBLICATIONS

The European Search Report dated Jun. 14, 2021 for European Application No. 201315507.2.

* cited by examiner

84: External Interface Circuit
86: Internal Interface Circuit

84: External Interface Circuit
86: Internal Interface Circuit

84: External Interface Circuit
86: Internal Interface Circuit

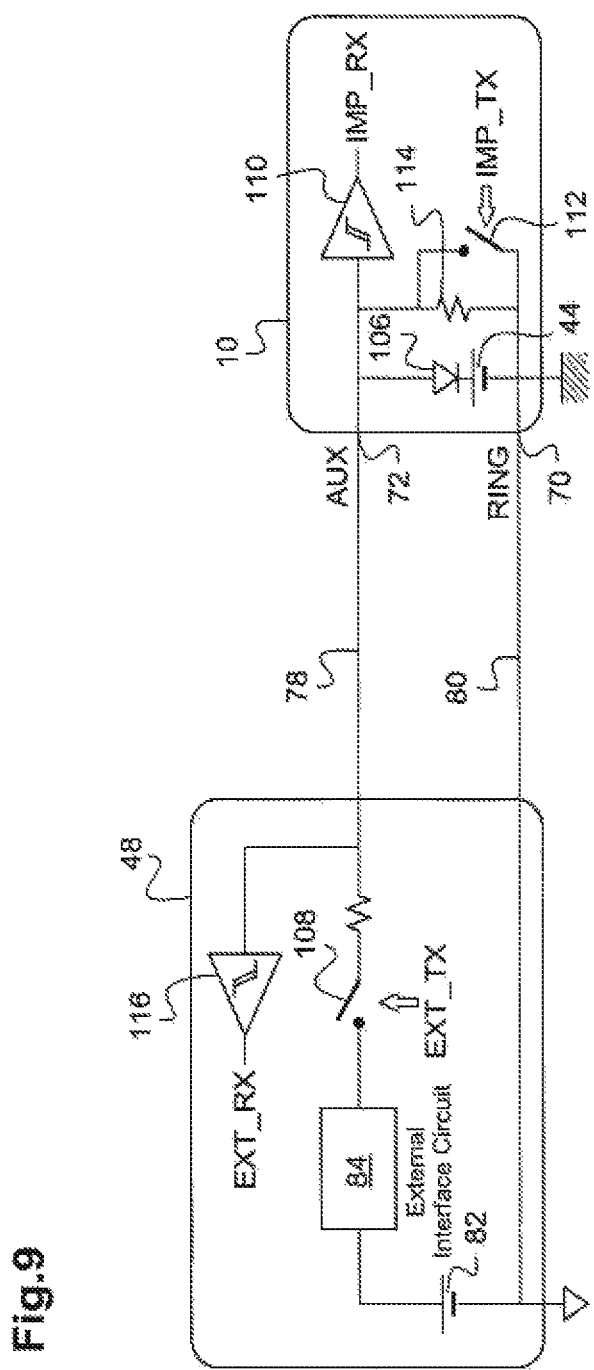

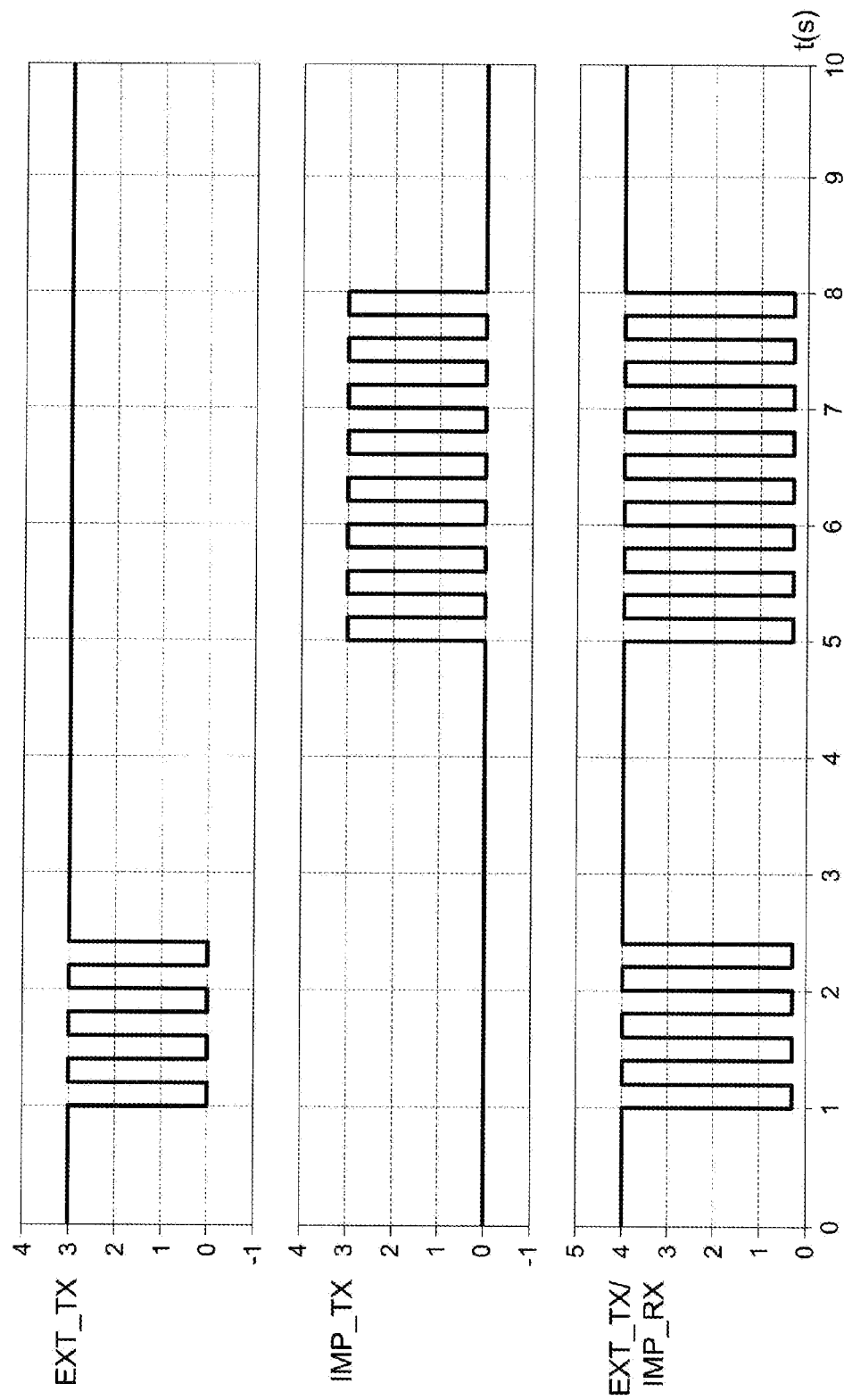

AUTONOMOUS CARDIAC IMPLANT OF THE LEADLESS CAPSULE TYPE, COMPRISING AN INTERFACE FOR EXTERNAL COMMUNICATION DURING TRANSPORTATION AND STORAGE

BACKGROUND OF THE INVENTION

Technical Field

The invention relates to medical devices during their transportation and storage, in the period between their manufacturing and the moment where they are used by the practitioner to be implanted in a patient.

It more particularly relates to those devices which incorporate a self-powering system comprising a mechanical energy harvesting device, also called "harvester" or "scavenger", associated with an integrated energy storage component, such as a rechargeable buffer micro-battery or a high-performance capacitor.

The harvesting device can in particular be of the so-called "PEH" (Piezoelectric Energy Harvester) type, which uses as a mechanical-electrical transducer an oscillating piezoelectric beam coupled to an inertial mobile mass.

Transportation and storage of such devices involve, as will be explained hereinafter, a certain number of specific constraints and difficulties, related to the presence of the harvester, and that are not met with the conventional medical devices powered by a very long-life static battery (devices such as pacemakers, implantable defibrillators, etc.).

State of the Art

The "harvester" devices are used in particular to power autonomous implantable medical devices (hereinafter "implants"), in particular autonomous capsules designed to be implanted into a heart cavity.

The invention is nevertheless not limited to such a device, it is also applicable to many other types of miniaturized implantable medical devices, whatever the operational purpose thereof, cardiac or other.

One of the critical aspects of these miniaturized devices is the power autonomy. Indeed, life duration of such a device being about 8 to 10 years, taking into account the very small sizes, it is not possible to use a conventional battery, even a high-density one. A harvester addresses this drawback by collecting the mechanical energy resulting from the various movements undergone by the implant body. These movements may have for origin a certain number of phenomena occurring in particular at the rhythm of the heartbeats, such as periodic shakes of the wall on which the implant is anchored, heart tissue vibrations linked i.a. to closings and openings of the heart valves, or also blood flow rate variations in the surrounding environment, which stress the implant and make it oscillate at the rhythm of the flow rate variations. The mechanical energy that is collected is converted through a suitable mechanical-electrical transducer into an electrical energy (voltage or current) sufficient for powering the various circuits and sensors of the device and charging the energy storage component. This power system allows the device to operate in full power autonomy for its whole lifetime.

This energy harvesting technique is particularly well adapted for powering the implanted autonomous capsules having no physical connection with a remote device. Such capsules are called for this reason "leadless capsules", for distinguishing them from the electrodes or sensors arranged at the distal end of a lead, through the whole length of which run one or several conductors connected to a generator itself connected to the opposite, proximal end.

In the cardiac application case, the leadless capsule continuously monitors the patient's rhythm and if necessary issues to the heart electrical pulses for pacing, resynchronization and/or defibrillation in case of rhythm disorder detected by the capsule. The leadless capsule may be an epicardial capsule, fixed to the outer wall of the heart, or an endocavitary capsule, fixed to the inner wall of a ventricular or atrial cavity, or a capsule fixed to the wall of a vessel near the myocardium. The fixation of the capsule to the implantation site is made through a protruding anchoring system extending the capsule body and designed to penetrate the cardiac tissue, in particular by means of a screw.

The capsule comprises various electronic circuits, sensors, etc., as well as wireless communication transmission/reception means for the remote exchange of data, the whole being integrated in a body of very small size that can be implanted at sites whose access is difficult or that leave little space available, such as the apex of the ventricle, the inner wall of the atrium, etc.

US 2009/0171408 A1 (Solem), US 2017/0151429 A1 (Regnier) and WO 2018/122244 A1 (Regnier) describe various examples of such intracardiac leadless capsules.

The energy harvesting device integrated to these capsules can in particular implement an inertial pendular unit subjected to the above-described external stresses. A mobile mass (called "seismic mass") coupled to an elastically deformable element is driven according to the movements of the capsule and vibrates at a natural free oscillation frequency. The mechanical energy of the oscillation is converted into electrical energy by a mechanical-electrical transducer that is, in the case of a PEH, a piezoelectric component such as a beam clamped at one of its ends and coupled to the inertial mass at its other end, which is free. The beam, that is cyclically and alternately stressed in bending, generates electrical charges that are collected at the surface of the component to be used by the self-powering system of the capsule for powering the various electronic circuits and sensors, and for charging the buffer micro-battery.

Such an energy harvesting device of the PEH type for powering an implant from the oscillations of a piezoelectric beam is described in particular in U.S. Pat. No. 3,456,134 A (Ko) and in WO 2019/001829 A1 (Cairdac) and EP 3 708 221 A1 (Cairdac).

In the pre-implantation phase, i.e. during transportation and storage of the implant, it is however necessary to maintain during the whole storage duration (which may last several months) a sufficient charge level of the integrated buffer micro-battery to maintain the electric circuits of the implant in standby state until the moment of implantation, moment at which these circuits will be activated to become fully functional.

Of course, the consumption of the implant in standby state is very low, of the order of 100 nA, including the power supply of the standby circuits and the self-discharge current of the energy storage component. But the energy storage components used with the miniaturized implants, whether they are rechargeable buffer micro-batteries or high-capacity capacitors (hereinafter, the generic term "battery" will be used), have a limited capacity, typically with a value of the order of 1 mAh to 10 mAh, which ensures a shelf life of about 1000 hours in the worst case, i.e. approximately 40 days only—indeed, on shelf, the implant is stationary and there is therefore no charge by the harvester.

These values are to be compared to the traditional implants' ones (pacemakers, implantable defibrillators, etc.) provided with a long-life static battery, whose capacity is generally of at least 100 mAh: in this case, for a same standby current of 1 µA, after 20 months of storage the battery will have lost only 15% of its nominal capacity.

U.S. application Ser. No. 17/463,996 filed on Sep. 1, 2021 and assigned to the present applicant, hereby incorporated by reference, for an "Accessory for transportation and storage of an autonomous cardiac implant of the leadless capsule type", describes a means for ensuring the power supply of implant standby circuits in a state in which the implant is immobile, hence without operation of the harvester (storage on a shelf before implantation), and that during a very long duration, typically at least 24 months. Essentially, the capsule is galvanically coupled to an external source of electrical energy physically separated from the implant, for example a battery housed in the same package as that in which the implant is packaged. The external source is coupled to the implant rechargeable battery in such a way as to ensure a power supply of this rechargeable battery by the external source and hence to maintain, during the whole transportation and storage duration before implantation, a battery charge level higher than a predetermined minimum level.

A comparable configuration is described by WO 98/08567 A1 (Pacesetter), in which the implant is coupled to an external source of energy for powering the implant during the whole storage duration, thus preserving the internal power battery of the latter. An interface circuit makes it possible to switch at will the power supply of the implant circuits, either to the external source or to the internal battery.

However, in this configuration, there is a first problem, i.e. the way to ensure, outside the capsule, the galvanic coupling of the external source to the capsule and, inside the capsule, up to the rechargeable battery.

The matter is in particular to guarantee that, once the capsule implanted and fully functional in order to fulfill the required functions, in particular cardiac potential detection/pacing, the means previously implemented to maintain the battery charge level during the storage won't have any incidence on the implant operation, and won't create any risk of hardware or software dysfunction.

A second problem lies in the multiplication of the implant external electrodes due to the function of battery charging in storage configuration. The galvanic coupling of the external source of electrical energy (the cell within the implant package) to the rechargeable battery inside the implant indeed requires to establish a physical contact with electrodes present at the surface of the implant tubular body.

It is of course possible to add on the tubular body electrodes (conductive surfaces) exclusively dedicated to the battery charging function, but this solution complicates the mechanical design of the implant, in particular its tubular body consisted of a welded assembly of conductive metal parts (generally titanium) and electrically insulating parts (generally ceramic). An increase in the number of electrodes would then result in a multiplication of the number of parts to be assembled or the number of welds, with consequently an increase of the difficulty of realization and an increase of the cost of manufacturing.

Moreover, a third problem results from the necessity to maintain, even during the storage, the possibility to exchange data between, on the one hand, the capsule in its dormant state and, on the other hand, the external environment: indeed, before any implantation, it is necessary that a communication can be established with the capsule to "wake it up" from its dormant state, check the internal battery charge level, test the capsule before implanting it to ensure that there is no functional anomaly, adjust the setting of the detection/pacing circuits to adapt them to the patient's clinical state, etc.

On this matter, US 2019/070422 A1 (Regnier) describes a leadless capsule provided with means for communication before implantation, i.e. in a situation in which it is still configured for storage and transportation. The exchange of data between the capsule and the external environment lies on an intracorporeal communication technique called HBC (Human Body Communication), which is a technique in which the communication is conducted through a medium consisting of the body tissues or interstitial fluids of a patient and can therefore normally only be implemented after implantation. The document proposes to add to the capsule an accessory nevertheless allowing the use of a capacitive coupling (galvanically isolated) between the capsule and an external casing to exchange data using this way while the capsule is not yet implanted.

Another communication technique consists in exchanging data by wireless RF transmission (Bluetooth BLE telemetry signals or in the ISM bands).

But, in either case, the capsule is supposed to be already in a fully functional state, and not in a dormant state required by an extended storage.

SUMMARY OF THE INVENTION

To solve the above-mentioned problems, the invention proposes an autonomous cardiac implant of the leadless capsule type, of a known type described in particular by the above-mentioned EP 3 708 221 A1, comprising: a tubular body; surface electrodes carried by the tubular body; an energy harvesting module adapted to convert external stresses applied to the implant into electrical energy, comprising an inertial pendular unit including an elastically deformable element coupled to an inertial mass; a rechargeable battery adapted to be charged by the energy harvesting module, the battery being previously charged to an initial charge level; and an interface circuit adapted to selectively couple the surface electrodes to the rechargeable battery.

The interface circuit of this implant comprises a switching circuit adapted to operate a switching between: (i) a transport and storage configuration in which, before implantation of the implant, the surface electrodes are connected to a link coupling to an external source forming an electrical energy reserve, the external source being physically separated from the implant, the interface circuit being adapted, in this transport and storage configuration, to receive a power supply from the external source and to release this power supply to the rechargeable battery; and (ii) a functional configuration, in which the surface electrodes are decoupled from the external source after the implant has been implanted.

According to a first characteristic aspect of the invention, at least one of the implant surface electrodes is an auxiliary electrode that is not a cardiac potential detection/pacing electrode, and in the transport and storage configuration, the interface circuit couples the auxiliary electrode to the implant rechargeable battery, whereas, in the functional configuration, the interface circuit decouples the auxiliary electrode from the implant rechargeable battery and put the auxiliary electrode to a floating potential.

Very advantageously, the switching circuit is a circuit adapted to operate an irreversible switching from the transport and storage configuration to the functional configuration, in particular thanks to a component of the One-Time Programmable, OTP, type, with at least one MOS switch whose gate is controlled by this OTP component.

Preferably, at least one of the surface electrodes is a cardiac potential detection/pacing electrode, in particular a ring electrode of the implant. In this case, in the transport and storage configuration, the interface circuit couples the detection/pacing electrode to the implant rechargeable battery and decouples the detection/pacing electrode from a detection/pacing circuit of the implant; and, in the functional configuration, the interface circuit couples the detection/pacing electrode to the implant detection/pacing circuit and decouples the detection/pacing electrode from the implant rechargeable battery.

According to a second characteristic aspect of the invention, the implant comprises a data transmitter circuit adapted, in the transport and storage configuration, to send communication signals, via the surface electrodes, on the link coupling to the external source.

The communication signals can in particular be OOK modulated signals, the data transmitter circuit comprising a circuit adapted to modulate the implant charging impedance viewed from the link coupling to the external source.

The communication signals output by the transmitter circuit can transmit data such that: rechargeable battery voltage; implant internal parameters; and implant status.

In the same way, the implant can comprise a data receiver circuit adapted, in the transport and storage configuration, to receive, via the surface electrodes, communication signals transmitted on the link coupling to the external source.

The communication signals can in particular be signals OOK modulated by pulse cuts of the coupling link, the data receiver circuit comprising a demodulation circuit detecting pulse cuts of the power supply received from the external source. The communication signals received by the receiving circuit can transmit data such that: implant internal parameters change; and transport and storage configuration to functional configuration switching control.

BRIEF DESCRIPTION OF THE DRAWINGS

FIG. 9 is a functional electrical diagram explaining how a two-directional communication is established between the capsule and the external environment with the galvanic coupling intended for recharging the buffer battery by means of an external cell.

FIG. 10 illustrates examples of signals exchanged with the electrical configuration of FIG. 9.

DETAILED DESCRIPTION OF PREFERRED EMBODIMENT OF THE INVENTION

Figure 1:
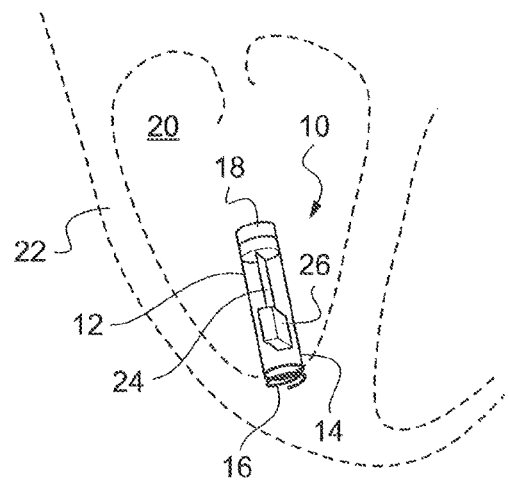
FIG. 1 illustrates a leadless capsule in its environment, implanted in the bottom of the right ventricle of a patient's myocardium.
Figure 2:
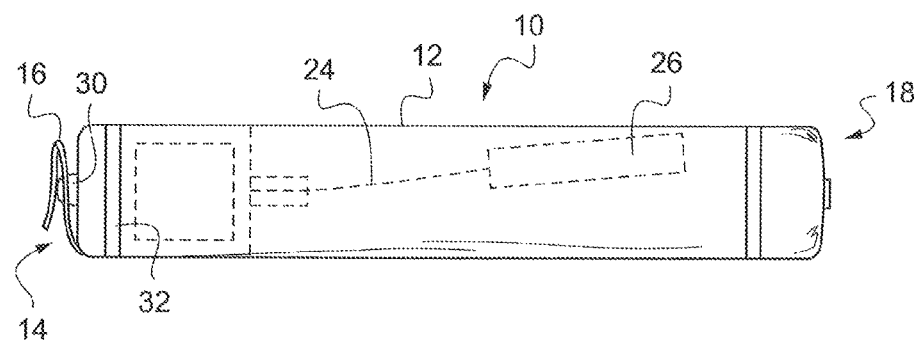
FIG. 2 is a longitudinal general view of a leadless capsule comprising a pendular unit based energy harvester.

In FIGS. 1 and 2 is shown an implant of the leadless capsule type 10 in an application to cardiac pacing.

Capsule 10 has the external form of an elongated cylindrical tubular body 12 enclosing the various electronic and power circuits of the capsule, as well as a pendular unit based energy harvester. The typical size of such a capsule is about 6 mm diameter for about 25 to 40 mm length.

Tubular body 12 has, at its front (distal) end 14, a protruding anchoring element, for example an helical screw 16, to hold the capsule on the implantation site. The opposite (proximal) end 18 of capsule 10 is a free end, which is only provided with means for the temporary connection to a guide-catheter (not shown) or another implantation accessory used for implantation or explantation of the capsule.

In the example illustrated in FIG. 1, the leadless capsule 10 is an endocavitary implant implanted into a cavity 20 of myocardium 22, for example at the apex of the right ventricle. As an alternative, still in an application to cardiac pacing, the capsule can also be implanted on the interventricular septum or on an atrial wall, or also be an epicardial capsule placed on an external region of the myocardium.

Leadless capsule 10 is moreover provided with an energy harvesting module comprising an inertial pendular unit that oscillates, inside the capsule, following the various external stresses to which the capsule is subjected. These stresses may result in particular from: movements of the wall to which the capsule is anchored, which are transmitted to tubular body 12 by anchoring screw 16; and/or blood flow rate variations in the environment surrounding the capsule, which produce oscillations of tubular body 12 at the rhythm of the heartbeats; and/or various vibrations transmitted by the heart tissues. The pendular unit can in particular be consisted of a piezoelectric beam 24 clamped at one of its ends, and whose opposite, free end is coupled to a mobile inertial mass 26, the whole forming a pendular system of the mass-spring type. Due to its inertia, mass 26 subjects beam 24 to a deformation of the vibratory type on either side of a neutral or non-deformed position corresponding to a stable rest position in the absence of any stress. Piezoelectric beam 24 further performs a mechanical-electrical transducer function for converting the mechanical bending stress that is applied to it into electric charges that are collected to produce an electrical signal that, after rectification, stabilization and filtering, will power the various electronic circuits of the capsule.

Figure 3:
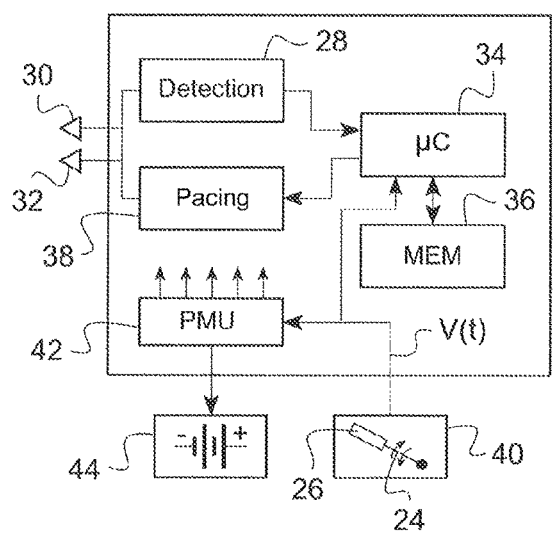
FIG. 3 schematically shows the main functional blocks constituting a leadless capsule.

FIG. 3 is a synoptic view of the various electric and electronic circuits integrated to the leadless capsule, presented as functional blocks.

Block 28 denotes a heart depolarization wave detection circuit, which is connected to a cathode electrode 30 in contact with the heart tissue and to an associated anode electrode 32, for example a ring electrode formed on the tubular body of the capsule (see FIG. 2). Detection block 28 comprises filters and means for analog and/or digital processing of the collected signal. The so-processed signal is applied to the input of a microcomputer 34 associated with a memory 36. The electronic unit also includes a pacing circuit 38 operating under the control of microcomputer 34 to issue, as needed, myocardial pacing pulses to the system of electrodes 30, 32.

An energy harvesting circuit PEH 40 is moreover provided, consisted by the pendular unit formed by piezoelectric beam 24 and inertial mass 26, described hereinabove with reference to FIGS. 1 and 2. Piezoelectric beam 24 also ensures a mechanical-electrical transducer function that converts into electrical 10 charges the mechanical stresses undergone and produces a variable electrical signal V(t), which is an alternating signal oscillating at the natural oscillation frequency of the pendular beam 24/mass 30 unit, and at the rhythm of the successive beats of the myocardium to which the capsule is coupled.

The variable electrical signal V(t) is sent to a power management unit or PMU 42. PMU 42 rectifies and regulates the signal V(t) so as to output a stabilized direct voltage or current used to power the various electronic circuits and to charge an integrated buffer micro-battery 44 (to the case of a micro-battery will be equated that of a high-capacity capacitor, which fulfils the same function of temporary storage of an electrical energy for ensuring the power supply of all the circuits of the implant).

Figure 4:
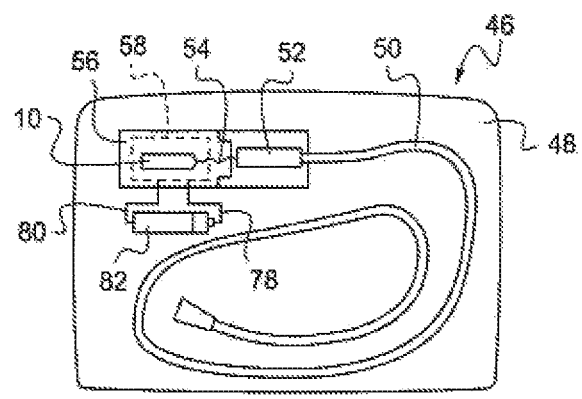
FIG. 4 is a general view illustrating the full packaging, with the implant and its accessories enclosed in a sterile sealed package.

FIG. 4 is a general view illustrating the full packaging, with the implant and its accessories enclosed in a sterile sealed package.

The packaging comprises a sealed package 46 defining a sealed and sterile internal volume 48, in which capsule 10 is enclosed. The package also contains, in addition to the capsule, a catheter 50 for the implantation, which is ended, on the distal end (near the capsule), by a "housing" 52 receiving and protecting the capsule during the guiding into the venous network and also preventing anchoring screw 16 to injure the vessel walls. In the package, the capsule is out of housing 52 and is connected to the catheter only by a security thread or "Ariane's thread" 54, from which it will be disconnected only once the definitive implantation reached.

Figure 5:
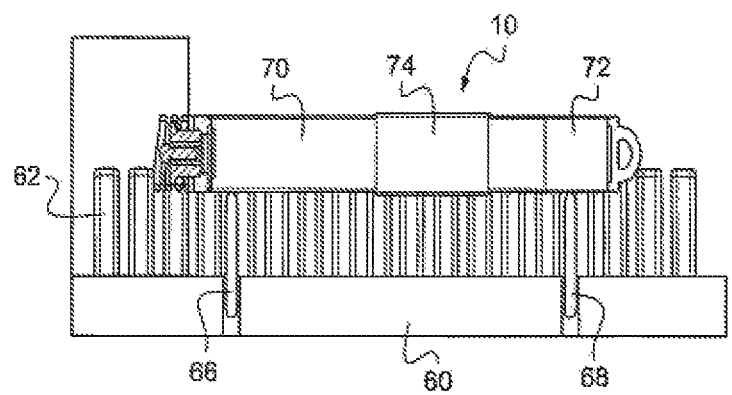
FIG. 5 is an elevation view, in partial cross-section, of the implant placed on its protection and wedging support, in situation during the transportation and the storage.

Capsule 10 is arranged inside a protection and wedging support 56, including an absorbing structure 58 comprising, for example, as illustrated in FIG. 5, a part 60 supporting a texture of deformable flexible strands or slats 62 or, as an alternative, a massive block of foam.

Figure 6:
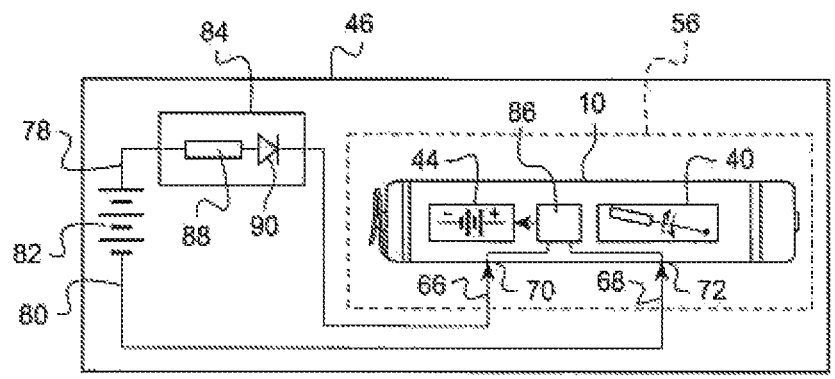
FIG. 6 is an electrical diagram explaining how the system for recharging the implant buffer battery operates.

In addition to the mechanical protection, it is provided to establish an electrical coupling with electrodes of the capsule, in such a way as to be able to charge as needed the buffer battery integrated to the capsule, as will be explained hereinafter with reference to FIG. 6.

For that purpose, touch tips 66, 68 are provided, coming into contact with distinct conductive surfaces 70, 72 of the tubular body 12 of capsule 10.

Such a tubular body structure comprising two conductive (metallic) surfaces 70, 72, separated by an isolating (ceramic) cylindrical surface 74, is described for example in EP 3 730 185 A1 (Cairdac), to which reference may be made for more details.

Touch tips 66, 68 may be rods with a telescopic end or a retractable ball coming into contact with conductive surfaces 70, 72; as an alternative, the electrical coupling may be made through flexible blades or conductive springs, or through any other means fulfilling the same function.

Touch tips 66, 68 are connected by respective conductors 78, 80 to a source of electrical energy 82 (FIG. 4), offset with respect to the capsule protection and wedging support 56.

The source of electrical energy can be a conventional cell, for example of 1.5 V. As an alternative, the offset source of electrical energy can be an inductive energy receiver, for example an inductive charging loop placed in the internal volume 48 of the sterile packaging of package 46; this loop is then coupled to an inductive energy emitter located outside the sterile packaging 46.

The way the charge level of the buffer battery 44 can be maintained at a satisfying minimum level despite the absence of charge by harvester 40 will now be described with reference to the electrical diagram of FIG. 6.

Touch tips 66, 68 ensure a galvanic coupling of capsule 10 to the offset source of electrical energy 82 (hereinafter called "cell" for the sake of simplicity).

The nominal voltage of cell 82 is chosen in such a way as to be higher than the operational voltage of buffer battery 44, for example a cell voltage of 1.5 to 9 C, typically of 5 to 6 V, for a buffer battery voltage typically varying between 3 V and 4.2 V. If the cell voltage is lower than that of the buffer battery, a voltage booster circuit can be provided, either external to the capsule, or internal to the latter (for example, a voltage boost stage within PMU 42 (FIG. 3)).

The coupling of cell 82 to buffer battery 44 comprises, in addition to touch tips 64, 66, an interface circuit 84 between cell 82 and capsule 10, and an interface circuit 86 internal to the capsule for coupling the external conductive surfaces 70, 72 to buffer battery 44.

In its simplest configuration, the battery/capsule interface circuit 84 comprises a resistance 88 for limiting the charging current provided by the cell, and a diode 90 for interrupting the charging when the voltage level of battery 44 reaches the voltage value of cell 82. In a more elaborate alternative, the interface circuit 84 can comprise a circuit for determining the voltage level of the battery and controlling selectively the delivery of the charging current, by interrupting the power supply of battery 44 by cell 82 when the charge level exceeds a predefined high threshold, and by reestablishing this power supply when the charge level falls down to a predefined low threshold.

Moreover, a means can be provided, for example a LED (not shown), for visually controlling the correct coupling between cell 82 and capsule 10, i.e. for checking the good condition of the function of controlled charging of the capsule buffer battery by cell 82 inside the sealed packaging.

From a quantitative point of view, for a standby current and a self-discharge of the battery producing a permanent current of the order of 1 μA and for a capacity of the battery of the order of 1 mAh, a shelf life of about 1000 h, i.e. about 40 days, is normally obtained, due to the absence of charge by the harvester, which is immobile.

To guarantee a storage duration of 24 months during which the capsule must remain functional although being in standby state, it is necessary to provide for about 30 charge cycles of battery 44 by cell 82. With an estimated operation efficiency of 50%, the external cell 82 has a capacity of 60 mAh, a value fully compatible with that provided by the conventional "button" cells, which have typically a capacity of the order of 80 to 100 mAh or more.

It is hence possible to guarantee, with very simple means, in any circumstances, a very long term shelf storage, without any reduction of longevity of the capsule, the latter being always functional and ready to be awake at any time for its implantation.

Figure 7:
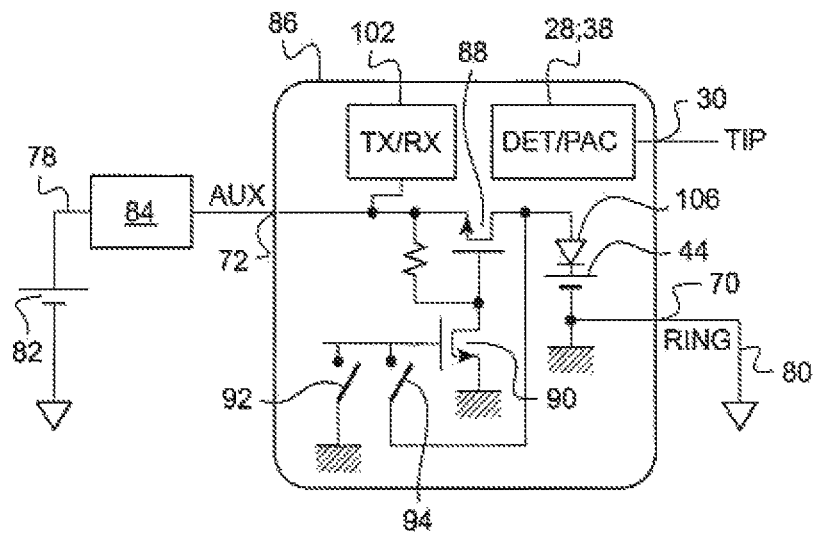
FIG. 7 illustrates an exemplary circuitry for ensuring inside the capsule an interface between the surface electrodes and the buffer battery for the temporary coupling of the latter to an external cell, in the case in which the capsule is of the type based on pacing by application of negative pulses to an end electrode.

FIG. 7 illustrates an exemplary circuitry for ensuring interface between the capsule surface electrodes and the external cell 82 via the galvanic coupling comprising the linking conductors 78, 80.

In this example, one of the electrodes is advantageously (but not limitatively) a pre-existing ring electrode of the capsule, acting as an anode electrode for the detection/pacing. This electrode is for example ring electrode 32 illustrated in FIG. 2, or ring electrode 70 illustrated in FIG. 5. It will be hereinafter denoted electrode RING. The other stimulation electrode, hereinafter denoted electrode TIP, is an end electrode such that cathode electrode 30 illustrated in FIG. 2. This distal electrode is usually covered with a coating of the titanium nitride type of very small thickness, very efficient as regards the pacing but very fragile and sensitive to scratches and particulate contaminations; it is that way preferable to reserve it to the sole pacing function by avoiding any contact with, for example, a touch tip as in the case of ring electrode 70 (touch tip 66 in FIG. 5).

The capsule is provided with an additional surface electrode, hereinafter denoted electrode AUX, for example electrode 72 illustrated in FIG. 5 in contact with touch tip 68, electrically insulated from electrode RING 70 by the electrically insulating, ceramic tubular part 74.

In the storage configuration, ring surface electrode AUX 72 is connected to the positive pole of external cell 82 by touch tip 68 and conductor 78, and ring electrode RING 70 is connected to the negative pole of external cell 82 by touch tip 68 and conductor 80.

Electrode AUX only serves to ensure the battery charging function described hereinabove with reference to FIG. 6; on the other hand, electrode RING has a double function: for the coupling to external cell 82 in order to charge the battery in the transport and storage phase, and as a pacing electrode (anode electrode) when the capsule is fulling functional, after implantation.

It is hence necessary to switch this electrode RING in such a way that the latter ensures this double role, by means of circuits that will now be described in more detail.

In the configuration illustrated in FIG. 7, the pacing mode used is the one most commonly encountered in practice, by emission of negative pulses applied to electrode TIP. For that purpose, electrode TIP is directly connected to detection/pacing circuits 28, 38, and electrode RING is connected to the ground of the capsule circuits.

The temporary coupling to external cell 82 is ensured during the storage by a transistor PMOS 88 connecting electrode AUX to buffer battery 44. The gate of this PMOS 88 is controlled by an NMOS 90, whose gate is connected to two parallel switches 92, 94, themselves connected to the ground of the capsule circuits and to the positive pole of buffer battery 44, respectively. In the transport and storage configuration, switch 92 is open and switch 94 is closed: the gate of NMOS 90 being put at a positive potential, NMOS 90 makes PMOS 88 passing, hence connecting the positive pole of buffer battery 44 to surface electrode AUX, and consequently to external cell 82 by coupling 78. The function of charging internal buffer battery 44 by external cell 82 can hence be ensured.

After implantation, the position of switches 92 and 94 is inverted, with switch 92 closed and switch 94 open. The gate of NMOS 90, grounded, blocks PMOS 88 and disconnects that way buffer battery 44 from electrode AUX. The two transistors MOS 88 and 90 being blocked, electrode AUX becomes floating and hence does not risk in any way to disturb the detection and pacing by circuits 28, 38 and electrodes TIP and RING.

Very advantageously, switches 92 and 94 are switches of the OTP (One Time Programmable) type, which are hence fusible components that maintain their closed or open state in any circumstances, in particular whatever the voltage of buffer battery 44 in operation. Especially, with such components, the transition from transport and storage configuration to final functional configuration will be an irreversible transition, guaranteeing that electrode AUX remains in the floating state for the remainder of the capsule life duration.

Figure 8:
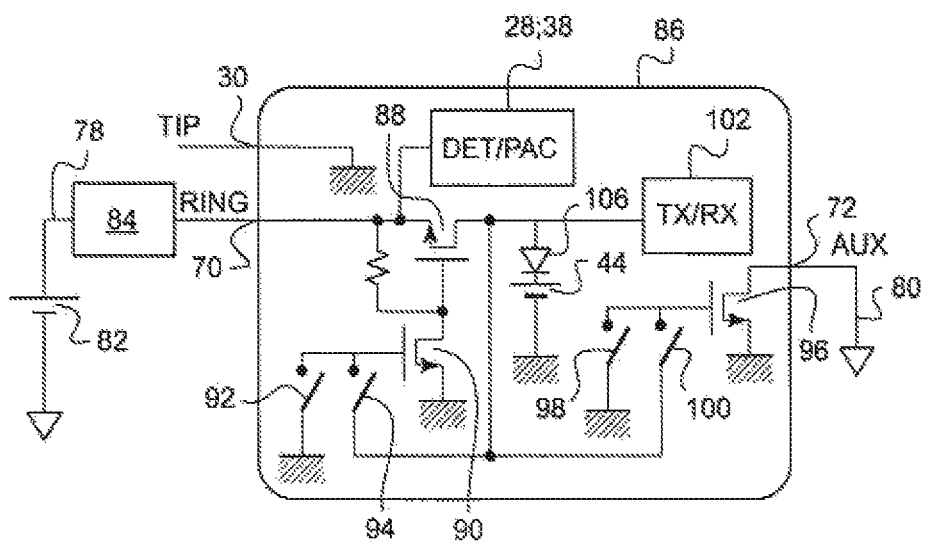
FIG. 8 illustrates an alternative of the circuitry of FIG. 7, intended for a capsule of the type based on pacing by application of positive pulses to a ring electrode.

FIG. 8 illustrates an alternative to FIG. 7, adapted to the cases of an implant with which the pacing is made through the application of positive pulses to ring electrode RING (and not by application of negative pulses to distal electrode TIP).

In this case, electrode TIP is permanently connected to the internal ground of the implant circuits, whereas electrode RING is connected to detection/pacing circuits 28, 38. In order to be able to control the two electrodes RING and AUX, an additional transistor NMOS 96 is provided, whose gate is driven by additional switches 98, 100 whose operation is the same as that of switches 92 and 94 previously described with reference to FIG. 7: during the transport and storage phase, switches 92 and 98 are open and switches 94 and 100 are closed, whereas, after implantation, switches 92 and 98 are closed and switches 94 and 100 are open, hence making electrode AUX fully and definitely floating. Switches 98 and 100 are advantageously, as switches 92 and 94, OTP components.

The way it is very advantageously possible to use the galvanic coupling existing between the capsule and the external cell not only to ensure the internal buffer battery charging, but also to make a bidirectional wired communication between the capsule and the external environment, will now be described.

As illustrated in FIGS. 7 and 8, the capsule comprises an internal transmitter/receiver circuit TX/RX 102, which is connected through diode 106 to the positive pole of buffer battery 44.

The equivalent diagram is that illustrated in FIG. 9 with, on the right, implant 10 and, on the left, its external environment, for example the environment of the sealed volume 48 of the transport and storage packaging 46.

The basic principle of the communication between the capsule and the external environment consists in exchanging brief voltage pulses:
  in the direction from the external environment to the capsule (the capsule then operating in reception), by short interruptions of the charging voltage applied to the buffer battery, and
  in the direction from the capsule to the external environment (the capsule then operating in transmission), by short modifications of the charging impedance of the capsule viewed from the outside.

On the external environment side, a switch 108 interposed between external cell 82 and the implant supply line 78 is controlled by a control signal EXT_TX. The resulting closings/openings of switch 108 produce very short cuts of the supply voltage applied to the capsule, which, due to their brevity, will be without incidence on the function of charging buffer battery 44.

FIG. 10 illustrates an exemplary alternative of control signal EXT_TX, as "all or nothing" amplitude-modulated voltage pulses (OOK), and the resulting signal IMP_RX that is detected by demodulator circuit 110 of capsule 10, this signal reflecting the voltage present on the coupling 78, 80 between external environment 48 and capsule 10.

On the capsule side, circuit TX/RX 102 comprises an internal switch 112 controlled by a control signal IMP_TX. When closed, switch 112 short-circuits a high-value resistance 114 mounted in parallel to internal battery 44 and diode 106, which has for effect to modify the charging impedance of capsule 10 viewed from the outside between i) a high value (value of the implant input impedance between terminals AUX and RING, switch 112 open) corresponding to a high logical signal and ii) a briefly lowered value (switch 112 closed) corresponding to a low logical signal. These variations of impendence are detected from the outside by demodulator circuit 116 that outputs a signal EXT_RX, this signal reflecting the voltage present on the coupling 78, 80 between external environment 48 and capsule 10.

As illustrated on the bottom chronogram of FIG. 10, signals can hence be exchanged on conductor 78, from the outside to the capsule (the first four pulses of the chronogram, produced by cuts of the charging supply) and, as an answer, from the capsule to the outside (the eight consecutive pulses, produced by the modulation of the charging impedance).

The information exchanged between the transport and storage of the capsule, before making the latter fully functional, can be very different, for example:
  from the outside to the capsule (signals EXT_TX): implant internal parameters adjustment, and transport and storage configuration to fully functional configuration switching control; and
  from the capsule to the outside (signals IMP_TX): voltage of the buffer battery 44, implant internal parameters, implant status.

The invention claimed is:

1. An autonomous cardiac implant of the leadless capsule type, comprising:
  a tubular body;
  surface electrodes carried by the tubular body;
  an energy harvesting module adapted to convert external stresses applied to the implant into electrical energy, comprising an inertial pendular unit including an elastically deformable element coupled to an inertial mass;
  a rechargeable battery adapted to be charged by the energy harvesting module, the battery being previously charged to an initial charge level; and
  an interface circuit adapted to selectively couple the surface electrodes to the rechargeable battery, comprising a switching circuit adapted to operate a switching between (i) a transport and storage configuration before implantation of the implant and (ii) a functional configuration after the implant has been implanted,
  wherein in the transport and storage configuration the surface electrodes are connected to a link coupling to an external source forming an electrical energy reserve, the external source being physically separated from the implant, and
  the interface circuit is adapted to receive a power supply from the external source and to release this power supply to the rechargeable battery, and
  wherein in the functional configuration, the surface electrodes are decoupled from the external source,
  wherein the implant further comprises at least one of:
  a data transmitter circuit adapted, in the transport and storage configuration, to send communication signals, via the surface electrodes, on the link coupling to the external source, and
  a data receiver circuit adapted, in the transport and storage configuration, to receive, via the surface electrodes, communication signals transmitted on the link coupling to the external source,
  and wherein a switch interposed between said external source and said link coupling to the external source is adapted to be controlled by a control signal for producing short cuts of a supply voltage of the power supply received by the capsule, whereby providing said communication signals.

2. The implant of claim 1, wherein the implant comprises said data transmitter circuit and the communication signals are OOK modulated signals and the data transmitter circuit comprises a circuit adapted to modulate an implant charging impedance as sensed from the external source.

3. The implant of claim 1, wherein the implant comprises said data transmitter circuit and the communication signals delivered by the transmitter circuit transmit data including at least one of: rechargeable battery voltage; implant internal parameters; and implant status.

4. The implant of claim 1, wherein the implant comprises said data transmitter circuit and the communication signals are signals OOK modulated by pulse interruptions of the coupling link, and the data receiver circuit comprises a demodulation circuit detecting pulse interruptions of the power supply received from the external source.

5. The implant of claim 1, wherein the communication signals received by the receiver circuit transmit data including at least one of: implant internal parameters change; and transport and storage configuration to functional configuration switching control.

6. The implant of claim 1, wherein the switching circuit is a circuit adapted to operate an irreversible switching from the transport and storage configuration to the functional configuration.

7. The implant of claim 6, wherein the switching circuit comprises at least one component of the One-Time Programmable, OTP, type.

8. The implant of claim 7, wherein the switching circuit comprises at least one MOS component whose gate is controlled by the OTP component.

9. The implant of claim 1, wherein at least one of the surface electrodes is a cardiac potential detection/pacing electrode, and wherein:
  in the transport and storage configuration, the interface circuit (i) couples the detection/pacing electrode to the implant rechargeable battery and (ii) decouples the detection/pacing electrode from a detection/pacing circuit of the implant, and
  in the functional configuration, the interface circuit (i) couples the detection/pacing electrode to the implant detection/pacing circuit and (ii) decouples the detection/pacing electrode from the implant rechargeable battery.

10. The implant of claim 9, wherein the detection/pacing electrode is a ring electrode of the implant.

11. The implant of claim 1, wherein at least one of the surface electrodes is an auxiliary electrode that is not a cardiac potential detection/pacing electrode, and wherein:
  in the transport and storage configuration, the interface circuit couples the auxiliary electrode to the implant rechargeable battery, and
  in the functional configuration, the interface circuit (i) decouples the auxiliary electrode from the implant rechargeable battery and (ii) puts the auxiliary electrode to a floating potential.

12. The implant of claim 1, wherein the implant comprises said data receiver circuit, and wherein said data receiver circuit includes a demodulator circuit adapted to detect said short cuts of the supply voltage of the power supply received by the capsule.

* * * * *